United States Patent [19]
Alscher et al.

[11] 4,149,019
[45] Apr. 10, 1979

[54] PROCESS FOR THE TRANSALKYLATION OF NUCLEAR METHYLATED PHENOLS

[75] Inventors: Arnold Alscher, Krefeld; Heinrich Steinke, Castrop-Rauxel; Gerd Collin, Duisburg; Günter Storch, Castrop-Rauxel, all of Fed. Rep. of Germany

[73] Assignee: Rütgerswerke Aktiengesellschaft, Frankfurt, Fed. Rep. of Germany

[21] Appl. No.: 839,484

[22] Filed: Oct. 4, 1977

[30] Foreign Application Priority Data

Oct. 9, 1976 [DE] Fed. Rep. of Germany ....... 2545770

[51] Int. Cl.$^2$ ............................................. C07C 37/12
[52] U.S. Cl. .................................................. 568/804
[58] Field of Search ........... 260/621 E, 624 C, 621 D, 260/624 R, 624 E; 568/804, 805

[56] References Cited

U.S. PATENT DOCUMENTS

| 3,417,149 | 12/1968 | Neuworth et al. | 260/621 D |
| 3,423,474 | 1/1969 | Anderson et al. | 563/780 |

FOREIGN PATENT DOCUMENTS

| 1813647 | 9/1970 | Fed. Rep. of Germany | 260/621 R |
| 1118287 | 6/1968 | United Kingdom | 260/621 D |

Primary Examiner—Werren B. Lone
Attorney, Agent, or Firm—Beveridge, DeGrandi, Kline & Lunsford

[57] ABSTRACT

A process for the transalkylation of nuclear methylated phenols into o-cresol in the liquid or gaseous phase is conducted in the absence of catalysts and in the presence of phenol.

4 Claims, No Drawings

PROCESS FOR THE TRANSALKYLATION OF NUCLEAR METHYLATED PHENOLS

BACKGROUND OF THE INVENTION

1 Field of the Invention

The present invention relates to a process for the transalkylation of nuclear methylated phenols into o-cresol in the liquid or gaseous phase, whereby particularly 2,6-dimethyphenol or a mixture of nuclear methylated phenols obtained, for example, as a residue in the case of an o-cresol synthesis, may be used as a starting material.

2. Description of the Prior Art

The synthesis residue obtained in the catalytic synthesis of o-cresol from phenol and methanol, which for the greatest part consists of 2,6-dimethylphenol (cf. German AS No. 1,256,755), frequently represents an undesirable and low grade by-product. The conversion into other valuable products, especially into o-cresol, which is needed for the production of herbicides in an increasing measure, is very valuable for economic reasons.

The isomerization and disproportionation of alkyl phenols in the liquid phase and gaseous phase have been known. However, the processes described hitherto were always based on the simultaneous use of catalysts. Thus oxidic catalysts, such as aluminum oxide, silicon-aluminum oxide as well as mixtures of silicon oxide with zirconium oxide or beryllium oxide, etc. are listed in several publications including German Patent No. 874,911; German Patent No. 1,014,550; German OD 1,956,383; U.S. Pat. No. 2,553,538; and British Patent No. 1,232,027. In all these cases, the reaction is not specific for o-cresol, but a mixture of numerous components is always obtained. Furthermore, in German OS No. 1,813,647, the use of an aluminum phenolate catalyst is described in the liquid phase reaction of a mixture of phenol and di-, tri- and polymethylphenols which, however, also only produces a partial conversion to o-cresol.

SUMMARY OF THE INVENTION

It has now been found that in processes according to the present invention, o-cresol may be produced at a good yield from 2,6-dimethylphenol or from a mixture of 2,6-dimethylphenol and other nuclear methylated phenols without the use of a catalyst. The conversion can be carried out with the addition of from 5% to 65% by weight of phenol both in the liquid phase as well as in the gaseous phase at elevated temperature and under pressure. If operating with a discontinuous or a continuous method of operation in the liquid phase, temperatures from 380° to 490° C., preferably from 420° to 470° C., at a pressure of 40 to 100 bar, and when operating in a continuous method of operation in the gaseous phase, temperatures from 450° to 650° C., preferably from 500° to 600° C., at a pressure of 15 to 60 bar, are required. The reaction times, depending on the selected method of operation, range from a few minutes for the gaseous phase reaction to several hours for the liquid phase reaction. In the continuous method of operation, the reaction products freed of o-cresol may be returned into the reactor.

DESCRIPTION OF THE PREFERRED EMBODIMENTS

The present invention provides a process for the transalkylation of nuclear methylated phenols into o-cresol in the liquid phase or in the gaseous phase, which process is chacterized in that the nuclear methylated phenols are subjected to conversion in the absence of catalysts and in the presence of from 5% to 65% by weight of phenol, based on the weight of the nuclear methylated phenols. When operating in the liquid phase, temperatures of 380° to 490° C., preferably from 420° to 470° C. at a pressure of 40 to 100 bar are used. When operating in the gaseous phase, temperatures of 450° to 650° C., preferably from 500° to 600° C. at a pressure of 15 to 60 bars are used. The reaction time for the liquid phase reaction will range from 1 to 8 hours and for the gaseous phase reaction will range from 2 to 40 minutes.

The invention will be explained in more detail on the basis of the following non-limiting examples. The proportion of the individual components was determined by means of gas chromatography. All parts are parts by weight unless otherwise specified.

EXAMPLES 1 AND 2

Phenol was added to a distillation residue from an o-cresol synthesis and the mixture (Composition A) was conducted in the gaseous phase continuously through a tube reactor at 550° C. (Example 1) or at 595° C. (Example 2). The pressure was maintained constant at 35 bar. The liquid volume rate (space velocity) amounted to $0.2[h^{-1}]$. Yields and compositions of the products freed of low boiling components and of phenol are listed in the following Table 1 under (I) and (II).

Table 1

|  | A | I | II |
|---|---|---|---|
| Reaction temperature [° C.] | — | 550 | 595 |
| Pressure [bar] | — | 35 | 35 |
| Yield [%] | — | 93.8 | 81.4 |
| Water [%] | 2.2 | — | — |
| Phenol | 5.1 | — | — |
| o-Cresol | 2.5 | 14.1 | 20.8 |
| m,p-Cresol | 5.1 | 3.3 | 5.7 |
| 2,6-Dimethylphenol | 61.1 | 42.5 | 23.2 |
| Residual dimethylphenols | 9.6 | 10.0 | 11.0 |
| Trimethylphenols | 9.3 | 10.6 | 6.1 |
| Tetramethylphenols | 2.9 | 2.6 | 1.1 |
| Pentamethylphenol | 2.2 | 0.3 | 0.1 |
| Higher boiling components | — | 3.7 | 13.5 |
| Residue | — | 12.9 | 18.5 |

Fractional distillation of the product thus obtained provided an o-cresol fraction clearly soluble in caustic soda solution.

EXAMPLES 3-5

Phenol was added to a distillation residue from an o-cresol synthesis and the mixture (Composition B) was conducted in the gaseous phase continuously through a tube reactor at 550° C. (Example 3), 600° C. (Example 4), and 570° C. (Example 5). In Examples 3 and 4, the pressure was maintained at 37 bar and in Example 5, at 20 bar; the liquid space velocity amounted to 0.25 $[h^{-1}]$. Yields and compositions of the transalkylation products liberated of phenol and low boiling components are listed in the following Table 2 under III, IV and V.

Table 2

|  | B | III | IV | V |
|---|---|---|---|---|
| Reaction temperature [° C.] | — | 550 | 600 | 570 |

Table 2-continued

|  | B | III | IV | V |
|---|---|---|---|---|
| Pressure [bar] | — | 37 | 37 | 20 |
| Yield [%] | — | 60.1 | 55.6 | 65.5 |
| Water [%] | 1.8 | — | — | — |
| Phenol | 38.8 | — | — | — |
| o-Cresol | 1.9 | 27.4 | 40.0 | 24.6 |
| m,p-Cresol | 3.6 | 6.2 | 9.0 | 5.2 |
| 2,6-Dimethylphenol | 36.3 | 36.1 | 20.3 | 31.5 |
| Residual dimethylphenols | 6.4 | 11.2 | 10.6 | 9.5 |
| Trimethylphenol | 7.1 | 7.3 | 4.3 | 6.2 |
| Tetramethylphenols | 2.1 | 1.9 | 1.3 | 1.8 |
| Pentamethylphenol | 1.8 | 0.3 | 0.5 | 0.2 |
| Higher boiling components | — | 5.3 | 11.8 | 6.3 |
| Residue | — | 4.3 | 2.2 | 14.7 |

An o-cresol clearly soluble in caustic soda solution was obtained by fractional distillation of the transalkylation product.

EXAMPLES 6-9

A starting mixture of composition B as in Examples 3-5 was placed into a stirring autoclave and was allowed to react for about 6 hours at 420° C. (Example 6), 435° C. (Example 7), 455° C. (Example 8) and 470° C. (Example 9). At the same time a pressure of 44 bar (Example 6), 42 bar (Example 7), 50 bar (Example 8) and 65 bar (Example 9) was maintained. Subsequently the mixtures were cooled, drained and the yields and compositions of the transalkylation products freed of phenol and low boiling components were determined as shown in the following Table 3 under VI-IX.

Table 3

|  | B | VI | VII | VIII | IX |
|---|---|---|---|---|---|
| Reaction temperature [° C.] | — | 420 | 435 | 455 | 470 |
| Pressure [bar] | — | 44 | 42 | 50 | 65 |
| Yield [%] | — | 68.2 | 75 | 76.1 | 76.4 |
| Water | 1.8 | — | — | — | — |
| Phenol | 38.8 | — | — | — | — |
| o-Cresol | 1.0 | 21.2 | 32.7 | 32.0 | 34.5 |
| m,p-Cresol | 3.9 | 5.5 | 5.4 | 5.2 | 6.5 |
| 2,6-Dimethylphenol | 36.6 | 40.8 | 22.6 | 19.8 | 13.2 |
| Residual dimethylphenol | 6.4 | 10.4 | 11.7 | 9.7 | 10.0 |
| Trimethylphenols | 7.1 | 8.2 | 6.3 | 5.3 | 3.9 |
| Tetramethylphenols | 2.1 | 2.9 | 1.8 | 1.3 | 0.8 |
| Pentamethylphenol | 1.8 | 1.0 | 0.4 | 0.4 | 0.2 |
| Higher boiling components | — | 5.5 | 6.1 | 13.1 | 17.0 |
| Residue | — | 4.5 | 13.0 | 13.2 | 13.9 |

The o-cresols obtained by fractional distillation of the transalkylation products were clearly soluble in caustic soda solution.

EXAMPLE 10

A mixture consisting of 278% phenol and 72.2% of 2,6-dimethylphenol was allowed to react in a shaking autoclave for 5 hours at 435° C. and 95 bar. After cooling, the reaction product was discharged and the non-reacted phenol was distilled off. The remaining mixture (yield 81.4%) had the following composition:

| o-Cresol | 25.8% |
|---|---|
| m,p-Cresol | — |
| 2,6-Dimethylphenol | 62.7% |
| Residual dimethylphenols | 0.5% |
| Trimethylphenols | 2.4% |
| Higher boiling components | 7.9% |
| Residue | 0.7% |

Fractional distillation of the product produced o-cresol clearly soluble in caustic soda solution.

What is claimed is:

1. A process for the translakylation of nuclear methylated phenols into o-cresol in the liquid phase which comprises subjecting 2,6-dimethylphenol or a mixture of nuclear methylated phenols obtained as a residue in an o-cresol synthesis to conversion in the absence of catalysts and in the presence of from 5% to 65% by weight of phenol based on the weight of the nuclear methylated phenols at a temperature of from 380° to 490° C. and at a pressure of from 40 to 100 bar.

2. The process according to claim 1 wherein the conversion is conducted in a discontinuous or continuous manner at a temperature of from 420° to 470° C.

3. A process for the translakylation of nuclear methylated phenols into o-cresol in the gaseous phase which comprises subjecting 2,6-dimethylphenol or a mixture of nuclear methylated phenols obtained as a residue in an o-cresol synthesis to conversion in the absence of catalysts and in the presence of from 5% to 65% by weight of phenol based on the weight of the nuclear methylated phenols at a temperature of from 450° to 650° C. and at a pressure of from 15 to 60 bar.

4. The process according to claim 3 wherein the conversion is conducted at a temperature of from 500° to 600° C.